(12) United States Patent
Kovacs et al.

(10) Patent No.: US 7,993,906 B2
(45) Date of Patent: Aug. 9, 2011

(54) CLOSED-LOOP ELECTRICAL STIMULATION SYSTEM FOR CELL CULTURES

(75) Inventors: Gregory T. A. Kovacs, Palo Alto, CA (US); R. Hollis Whittington, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1223 days.

(21) Appl. No.: 11/137,721

(22) Filed: May 24, 2005

(65) Prior Publication Data

US 2005/0282149 A1   Dec. 22, 2005

Related U.S. Application Data

(60) Provisional application No. 60/575,760, filed on May 28, 2004.

(51) Int. Cl.
*C12M 1/34* (2006.01)
(52) U.S. Cl. .................. 435/287.1; 435/7.21; 435/173.1
(58) Field of Classification Search .................. None
See application file for complete search history.

(56) References Cited

U.S. PATENT DOCUMENTS

| | | | | |
|---|---|---|---|---|
| 4,750,499 | A * | 6/1988 | Hoffer | 607/116 |
| 5,916,239 | A * | 6/1999 | Geddes et al. | 607/14 |
| 5,981,268 | A * | 11/1999 | Kovacs et al. | 435/287.1 |
| 6,114,164 | A | 9/2000 | Dennis et al. | 435/286.1 |
| 6,135,978 | A | 10/2000 | Houben et al. | 604/66 |
| 6,819,956 | B2 | 11/2004 | DiLorenzo | 607/45 |
| 7,294,333 | B1 * | 11/2007 | Feld et al. | 424/93.21 |

OTHER PUBLICATIONS

Doerr T. et al. Ionic currents contributing to the action potential in single ventricular myocytes of the guinea pig studied with action potential clamp, Pflugers Archiv Europian Journal of Physiology, 1990, vol. 416, pp. 230-237, entire document.*
DeHaan R.L. et al. Membrane response to current pulses in spheroidal aggregates of embryonic heart cells, The Journal of General Physiology, Feb. 1, 1975, vol. 65, pp. 207-222, entire document.*
Whittington R.H. et al. "A Multi-Parameter, Feedback-Based Electrical Stimulation System for Cardiomyocyte Cultures", Transducers '03; Downloaded from IEEE Xplore, The 12th International Conference an Solid State Sensors, Actuators and MicroSystems. Boston, Jun. 8-12. 2003, pp. 983-986.*
Solberg J. "Closed-Loop Control of Functional Electrical Stimulation for Human Gait: Introduction, Feedback Sensors, and Foreseeable Difficulties", A research report submitted for fulfilment of ELEC 8900 (full-time project) to the School of Electrical and Information Engineering, The University of Sydney on Nov. 15, 2000, total pp. 1-63.*
Daniel A. Wagenaar et al., "A versatile all-channel stimulator for electrode arrays, with real-time control," J. Neural Eng. 1 (2004) 39-45.
Steve M. Potter et al., "Long-Term Bidirectional Neuron Interfaces for Robotic Control, and In Vitro Learning Studies," Proceedings of the 25$^{th}$ Annual International Conference of the IEEE EMBS pp. 3690-3693, 2003.

* cited by examiner

*Primary Examiner* — Sue Liu
*Assistant Examiner* — Satyendra Singh
(74) *Attorney, Agent, or Firm* — Lumen Patent Firm

(57) ABSTRACT

The present invention provides a sensitive system for measuring the physiological response of an in-vitro cell culture to an environmental parameter. An electrical property of the cell culture is measured as a control signal, and a parameter of a stimulus is adjusted in real time to maintain the control signal at a specified value as the environment of the cell culture is altered, for example, pharmacologically. Artifact reduction and real-time control methods are two key aspects of preferred embodiments of the invention, and enable highly accurate determination of pulse parameters which elicit a desired response. Both aspects must be highly robust to the natural variations inherent in a biological system. This system is beneficial for studying the effects of environmental alterations because extremely small changes in the physiological response can be measured over time, revealing the magnitude and time-dependence of the impact of these alterations on the cell culture.

17 Claims, 10 Drawing Sheets

CLOSED-LOOP ELECTRICAL STIMULATION SYSTEM FOR CELL CULTURES

CROSS REFERENCE TO RELATED APPLICATIONS

This application claims the benefit of U.S. provisional application 60/575,760 filed on May 28, 2004, entitled "Closed-Loop Electrical Stimulation System for Cardiac Applications", and hereby incorporated by reference in its entirety.

GOVERNMENT SPONSORSHIP

This invention was made with support from DARPA under grant number N66001-99-C-8642. The US Government has certain rights in this invention.

FIELD OF THE INVENTION

This invention relates to stimulation of in vitro cell cultures.

BACKGROUND

Closed loop control methods have been utilized in various biological and medical applications. Early examples include functional electrical stimulation in electromyography, and rate-responsive pacemakers in cardiology. Further examples include prosthetic device control, neural network stimulation, drug delivery, and studies of arrhythmia, fibrillation and defibrillation. Closed loop control for in vivo control of an insulin pump or of pancreatic stimulation is considered in U.S. Pat. No. 6,135,978. Another example is U.S. Pat. No. 6,819,956, where in vivo closed loop control of all or part of a nervous system is considered. These studies generally relate to controlling a high-level biological function (e.g., an organ-level function), and are often related to in vivo applications. This emphasis on in vivo application of closed loop control is understandable in view of the direct applicability of such control methods to alleviate various medical conditions arising from functional deficiency.

Although in vitro closed loop control typically does not have the direct medical applications of in vivo control, it has also been considered in the art. More specifically, U.S. Pat. No. 6,114,164 relates to a system for controlling an in vitro muscle tissue specimen in order to emulate an in vivo environment. A significant motivation for this work is that certain kinds of muscle tissue specimens (e.g., skeletal muscle specimens) do not develop normally in vitro without application of mechanical forces to the specimen. The closed loop control considered in U.S. Pat. No. 6,114,164 includes an applied mechanical stimulus and/or a measured mechanical response within the control loop, thereby providing automatic adjustment of the mechanical environment of the sample to an appropriate level.

However, many in vitro studies do not relate to organ-level or tissue-level functional parameters as in the preceding examples. Instead, lower-level cellular responses (e.g., a response voltage) to electrical stimulation are often of interest. Application of known closed loop control methods (e.g., as in U.S. Pat. No. 6,114,164) to such situations can be complicated by practical issues, such as the selection of an appropriate control algorithm, and distinguishing stimulus artifacts from the response of interest. Distinguishing artifacts from real responses can be especially difficult when the stimulus is electrical and the response is also electrical.

Accordingly, it would be an advance in the art to provide closed-loop control of an electrically active cell culture having an electrical cellular response to a change in an environmental parameter in order to measure the effect of that environmental parameter on the cell culture.

SUMMARY

The present invention provides a system for measuring the response of an in-vitro cell culture to an environmental parameter. An electrical property of the cell culture is measured as a control signal, and a stimulus parameter such as stimulus pulse amplitude is adjusted in real time to maintain the control signal at a specified value as the environment of the cell culture is altered, for example, pharmacologically. Artifact reduction and real-time control methods are two key aspects of preferred embodiments of the invention, and enable highly accurate determination of pulse parameters which elicit a desired response. The artifact reduction technique utilizes techniques for establishing a reference potential for the cell culture and signal processing algorithms in order to accomplish detection of non-artifact events. A preferred control method includes monitoring the sign of the control signal error and its temporal behavior in order to achieve robust control and convergence upon the desired control signal with high accuracy in a noisy and highly quantized environment.

This system is beneficial in studying the effects of environmental alterations because extremely small changes in the physiological response can be measured over time, revealing the magnitude and time-dependence of the impact of these alterations on the cell culture. One example is the time-dependence and magnitude of changes in the pulse amplitude required to achieve 50% pacing while a cell culture is exposed to a drug that putatively impacts the excitability of the cells in the culture. Continuous determination of stimulation threshold amplitude during the altering of environmental parameters also has numerous applications to in vitro models of cardiac or other muscle type pacing.

DETAILED DESCRIPTION

Figure 1:
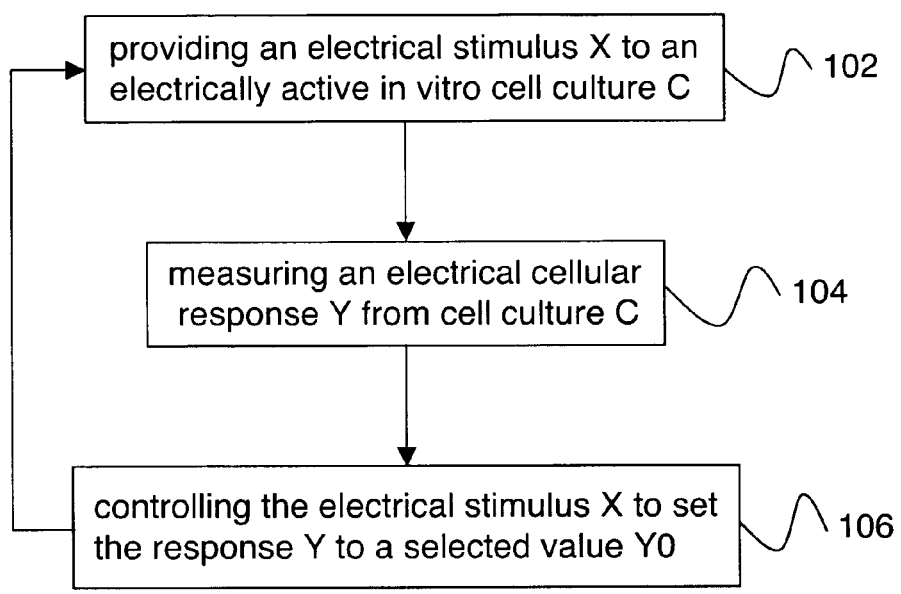
FIG. 1 is a block diagram of a closed loop cell culture control method according to an embodiment of the invention.

FIG. 1 is a block diagram of a closed loop cell culture control method according to an embodiment of the invention. Step 102 on FIG. 1 is providing an electrical stimulus X to an electrically active in vitro cell culture C. Step 104 is measuring an electrical cellular response Y from cell culture C. Step 106 is controlling the electrical stimulus X to set the cellular response Y to a selected value Y0. Since step 106 entails varying the stimulus X applied to cell culture C in step 102, this is a closed loop control method.

It is important to note that the cellular response Y in the present invention is an electrical cellular response, which poses unique problems. In particular, an electrical stimulus can interfere with accurate measurement of a cellular electrical response. Such interference is greatly reduced, or even eliminated entirely, if the cellular response is non-electrical (e.g., the mechanical cellular response of U.S. Pat. No. 6,114,164).

The present invention is applicable to closed loop control based on any electrical cellular response, including but not limited to: voltage waveform; current waveform; impedance; conduction velocity; conduction direction; conduction speed; and time delay between the stimulus and the electrical response. Here conduction velocity refers to the velocity (i.e. direction and speed) at which an electrical excitation propagates through a cell culture.

Any parameter of an electrical cellular response can also be regarded as an "electrical response" in practicing the invention. An example of such a parameter is efficacy of the stimulus for producing an electrical response, referred to as capture fraction. Thus the capture fraction is the fraction of the electrical stimuli that elicit a response from the cell culture. The electrical cellular response can be from part or substantially all of the cell culture. Some parameters, such as capture fraction, tend to relate to the entire cell culture, while other parameters, such as the voltage waveform, tend to relate to part of the cell culture.

The invention is applicable to any electrically active cell culture, including but not limited to: cardiac tissue, neural tissue, smooth muscle tissue, skeletal muscle tissue, pancreatic islet tissue and combinations thereof.

The electrical stimulus X is preferably provided in the form of charge-balanced pulses, to reduce undesirable electrochemical reactions at the stimulus electrodes. The stimulus X can be any electrical signal, and control of the stimulus can relate to any parameter of the stimulus. Such parameters include, but are not limited to: amplitude; duration; waveform; polarity; pulse rate; pulse train duration; multi-electrode timing; and multi-electrode spatial pattern. Some embodiments of the invention have only a single stimulation electrode, and other embodiments of the invention have multiple stimulation electrodes. In these multiple-electrode embodiments, the timing and spatial pattern of the stimulus are stimulation parameters that can be varied to control the cell culture.

Figure 2:
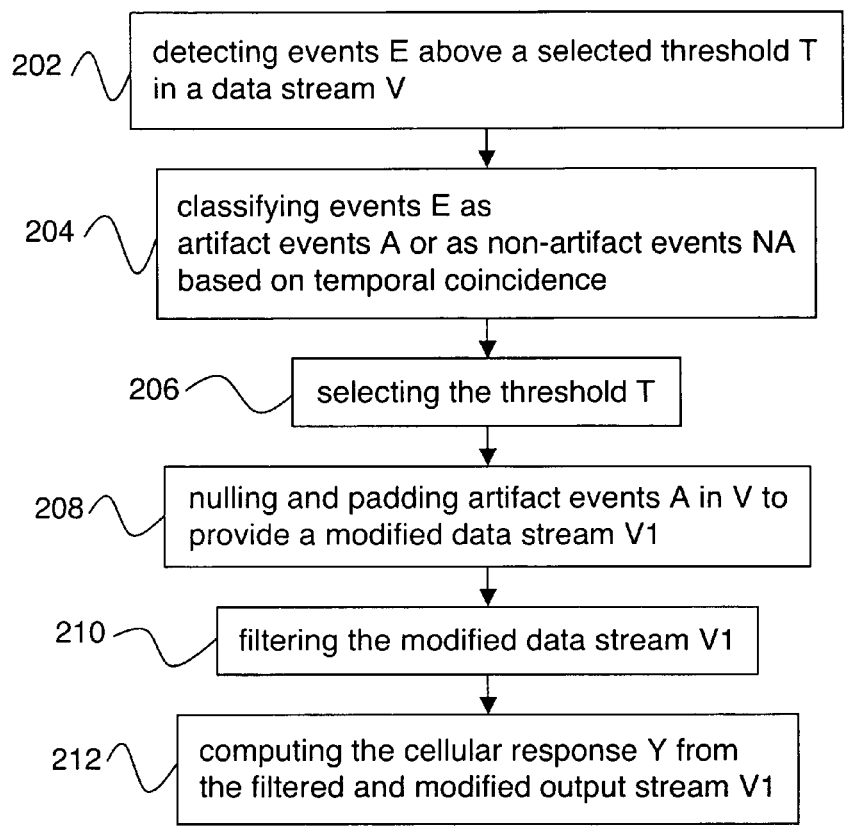
FIG. 2 is a block diagram of an artifact reduction method suitable for use with the invention.

FIG. 2 is a block diagram of an artifact reduction method suitable for use with the invention, e.g., as part of 104 on FIG. 1. Such artifacts in the measured electrical response are caused by the electrical stimulation. Accordingly, artifact reduction can be regarded as a method for reducing interference in a measured electrical response from an applied electrical stimulus. FIG. 2 relates to a signal processing method for reducing artifacts. Artifacts can also be reduced by appropriate electrode design, as considered in connection with FIG. 12.

Step 202 on FIG. 2 is detecting events E which are beyond a selected threshold T in a data stream V (e.g., above a positive threshold +T or below a negative threshold −T). This stage is for identifying all non-random events (i.e., including both artifact and non-artifact events) in data stream V. The non-artifact events are the cellular electrical responses of interest. The threshold T is used to distinguish events from random noise peaks. At this stage of the method, one or several thresholds can be employed. For example, in one experiment (hereinafter referred to as Experiment 1) relating to stimulation of cardiac myocytes, thresholds were set at ±90%, ±60%, and ±40% of the maximum data magnitude. In cases where several thresholds are used, steps 202 and 204 are carried out for each threshold, and step 206 entails choosing a single threshold to use for further processing (i.e., steps 208, 210, and 212).

Step 204 on FIG. 2 is classifying the events E as artifact events A or non-artifact events NA based on temporal coincidence. The idea behind this stage is that direct electrical interference tends to propagate through a cell culture much more rapidly than a cellular response.

For example, interference propagation times are typically <100 μs, while cellular response delays are typically greater than one ms, dependent on the conduction velocity. Therefore, temporal coincidence is suitable for separating A events from NA events. More specifically, several electrodes are used to measure cellular response. In this situation, an artifact will manifest as signals from some of the electrodes that fall within a narrow time window. In Experiment 1, a suitable artifact classification rule was to classify an event as an artifact if more than 30% of the corresponding electrode signals fall within a 0.5 ms window.

Step 206 on FIG. 2 is selecting the threshold. In some cases (e.g., if only one threshold is considered in step 202), step 206 is performed before step 202. More commonly, several thresholds are considered in steps 202 and 204, and then step 206 occurs after steps 202 and 204. The motivation for multiple thresholds is that the best threshold may not be known in advance. Thus events and artifacts can be identified using several "trial thresholds", one of which is selected to be the "real threshold" in step 206 based on the results of steps 202 and 204. In Experiment 1, the threshold (having the largest number of NA events was selected. If more than one trial threshold had a maximal number of NA events, the threshold having the smallest magnitude was selected.

Step 208 on FIG. 2 is nulling and padding the artifact events A in data stream V to provide a modified data stream V1. As indicated above, the signature of an artifact event A is one or more beyond-threshold values in the data stream V. These beyond-threshold values define a threshold window. However, the effect of an artifact event is not confined to the threshold window. Therefore, a nulling window including the threshold window is defined, and the values of V1 are set to zero in the nulling window. For example, in Experiment 1 the nulling window extended from 8 ms before the start of the threshold window to 2 ms after the end of the threshold window. The extent of the nulling window can be empirically determined to balance reduced loss of data (less nulling) with increased artifact removal (more nulling). The padding performed in step 208 is discussed in connection with step 210 below.

Step 210 on FIG. 2 is filtering the data stream V1. The purpose of filtering is to reduce the effect of the artifact remnants in V1 (i.e., the parts of the A events remaining after step 208). It is helpful to define a decay segment as a segment of V1 data immediately following the end of a nulling window. The name "decay segment" arises because the A remnants often have an exponential decay behavior. Thus the purpose of filtering is to remove the decay behavior from each decay segment. Brute force solutions such as curve fitting the decay and subtracting it off are possible, and can be regarded as filtering in a general sense. However, such approaches are not preferred because they can be computationally burdensome, and can be inaccurate for time-dependent artifacts.

Since the decay typically varies in time more slowly than the non-artifact response of interest, high-pass filtering is a preferred approach. However, simply passing the decay segment through a high pass filter is not preferred. One reason for this is that there is typically a discontinuity at the start of the decay segment between a non-zero first decay segment value and an (implied) value of zero for all times prior to the start of the decay segment. Such a discontinuity will cause a transient response in the filter output that can undesirably interfere with the NA response of interest. Another reason is that a high order digital filter relies on many samples of data to provide an accurate result. If the NA response is included in the first few samples, the filter will introduce unnecessary distortion. These problems can be avoided by extrapolating (e.g., by linear extrapolation) the decay segment to an earlier time than its "real" start time. This extrapolation is an example of the padding of step 208. Such padding increases the time separation between the effective start time of the decay segment and the non-artifact response of interest. In Experiment 1, a 10 ms linear extrapolation of the first 5 ms of each decay segment was performed, followed by filtering with a 100th order high pass least squares filter having a 40 Hz cutoff. The filter in this example required at least 100 samples of data to provide accurate results, and this 10 ms of padding provided the required number of data samples before processing the NA event.

Step 212 on FIG. 2 is computing the cellular response Y from the filtered data stream V1. The idea of this step is to put the pieces back together. More specifically, step 208 provides a filtered decay segment corresponding to each "original" decay segment in V1. The extrapolated part (if any) of each filtered decay segment is removed, so that it is the same length as the corresponding original decay segment. Then, each original decay segment is replaced with the corresponding filtered decay segment.

Figure 3:
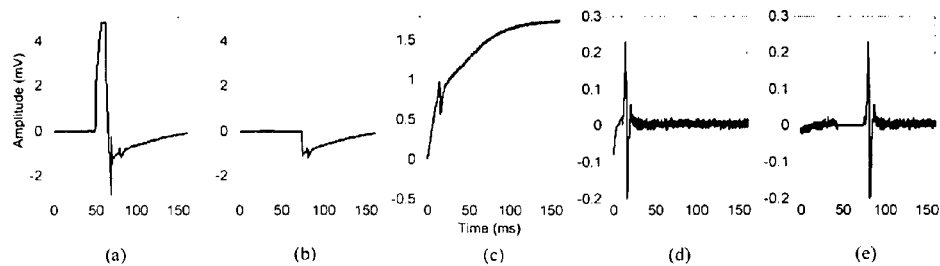
FIG. 3 shows exemplary results of intermediate steps of the method of FIG. 2.

FIG. 3 shows exemplary results of intermediate steps of the method of FIG. 2 for a typical artifact in the presence of a small amplitude, short-delay cellular response. Part (a) shows the original data. The large positive spike is the artifact, and the small signal at about 80 ms is the response of interest. Part (b) shows the data after nulling (step 208 above) has been completed. The signal of interest is seen to be a small deviation riding on an exponential decay curve. Part (c) shows the padded decay segment of the data of part (b), with linear extrapolation appended to the start of the decay segment. Part (d) shows the result of filtering the data of part (c), as in step 210 above. The dominant exponential behavior of part (c) is effectively removed. Part (e) shows the result of inserting the filtered data of part (d) into the nulled data stream of part (b), as in step 212 above. Comparison of part (e) to part (a) vividly demonstrates the magnitude of the problem often posed by artifacts, as well as the effectiveness of this method of the invention for artifact reduction.

Figure 4:
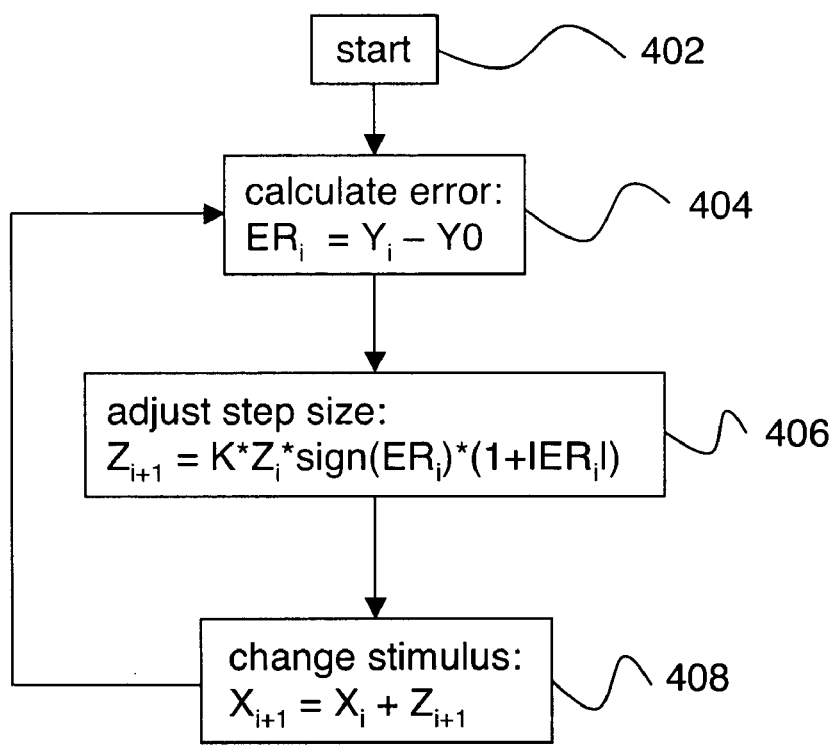
FIG. 4 shows a first stimulus updating algorithm suitable for use with the invention.

FIG. 4 shows a first stimulus updating algorithm suitable for use with the invention, e.g., as part of 106 on FIG. 1. This method is a modified proportional control method. More specifically, step 404 is calculation of an error ER, according to $ER_i=Y_i-Y0$, where $Y_i$ is the cellular response value at the ith iteration, and Y0 is the desired response value. Step 406 is adjusting a step size $Z_{i+1}$ according to $Z_{i+1}=K\ Z_i\ \text{sign}(ER_i)(1+|ER_i|)$, where K is a loop gain and $Z_i$ is the ith iteration step size. Hard upper and lower limits are also placed on the step size to make sure this parameter remains within a reasonable range. Step 408 is updating the stimulus according to $X_{i+1}=X_i+Z_{i+1}$. After step 408 is performed, step 404 follows, thereby closing the loop. The loop can be initialized at any convenient point, such as 402 on FIG. 4. Here the error signal is $1+|ER_i|$, as opposed to $|ER_i|$ as in a conventional proportional control loop. This modification improved loop stability in some cases.

Figure 5:
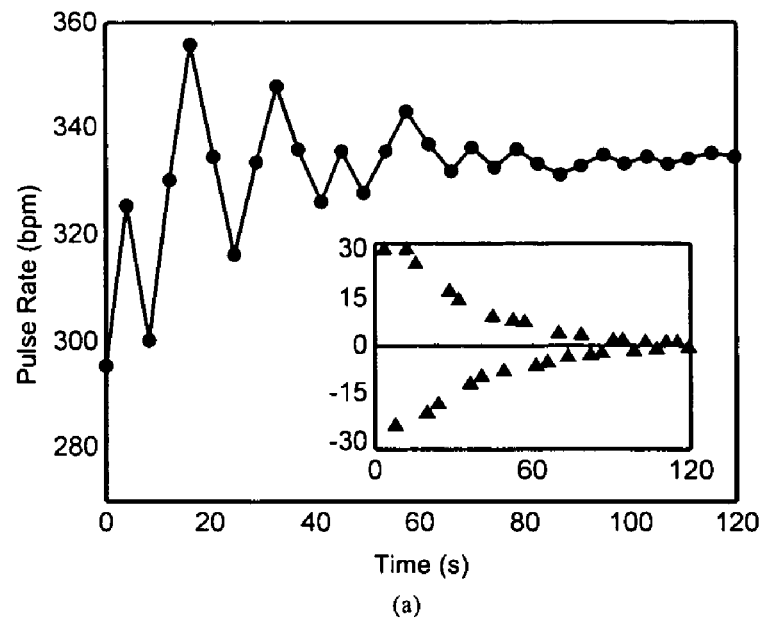
FIG. 5 shows measured results from an embodiment of the invention making use of the updating method of FIG. 4.
Figure 5:
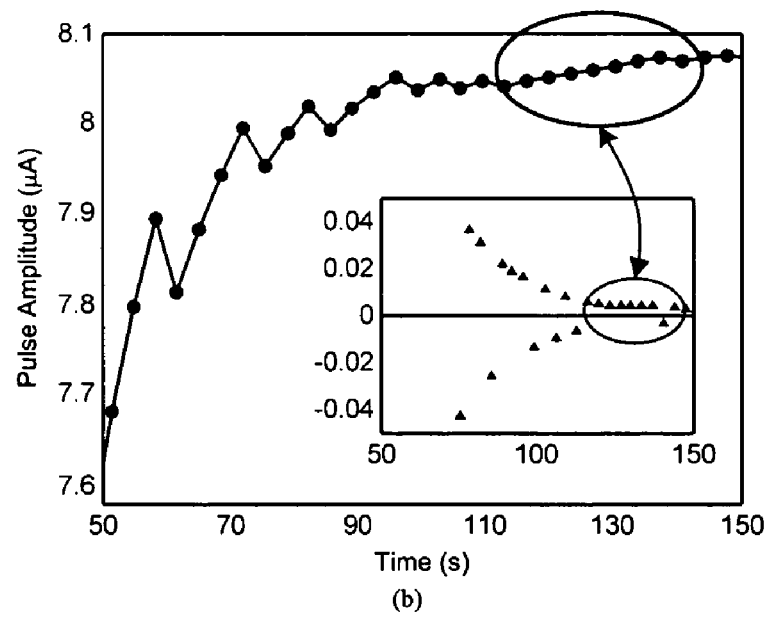

FIG. 5 shows measured results from an embodiment of the invention making use of the updating method of FIG. 4. In this experiment, the cellular response of interest was capture fraction, and the control loop set point was a capture fraction of 0.5. The main plot of part (a) relates to an experiment where the electrical stimulus control parameter is pacing rate, shown as a function of time, while the inset shows the step size as a function of time. The step size decreases smoothly from an initial value of 30 bpm to a final value of 0.6 bpm, and the pacing rate converges. The main plot of part (b) relates to an experiment where the electrical stimulus control parameter is pulse amplitude, shown as a function of time, while the inset shows the step size as a function of time. Convergence is also seen for part (b). The small shift seen on the circled area of part (b) is attributed to a change in culture parameters.

Figure 6:
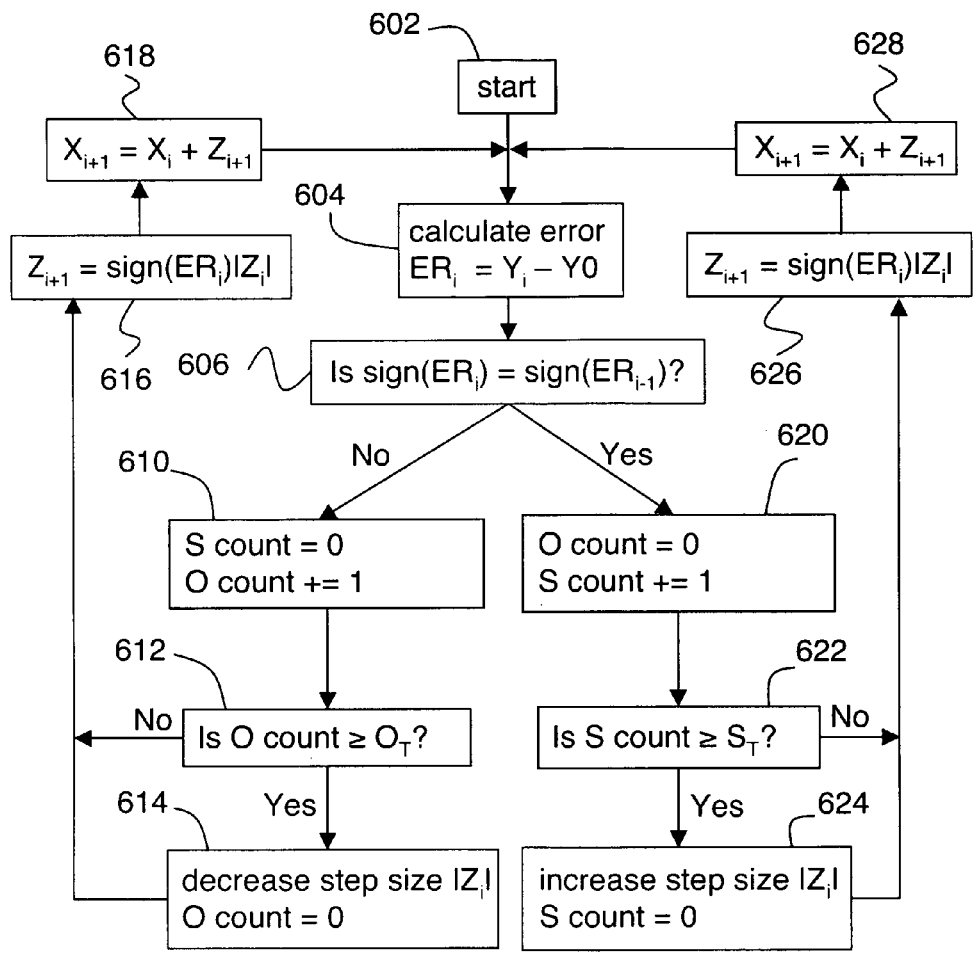
FIG. 6 shows a second stimulus updating algorithm suitable for use with the invention.

FIG. 6 shows a second stimulus updating algorithm suitable for use with the invention, e.g., as part of 106 on FIG. 1. Two main considerations motivate this method. The first consideration is that if the sign of the error remains constant for many consecutive iterations, then it is desirable to increase the step size in order to arrive at the control point more rapidly. The second consideration is that if the error alternates in sign for many consecutive iterations, then it is desirable to decrease the step size to provide more accurate control.

Step 604 is calculation of the error, as above. Step 606 is a comparison of the error sign at iteration i with the error sign at iteration i−1. This is the key step of the method of FIG. 6. Suppose that these two signs are the same. Processing then follows the "yes" path from step 606 to arrive at step 620. In step 620, an S (search) count is incremented by one, and an O (oscillation) count is reset to zero. The S count is the number of consecutive iterations having the same error sign, and the O count is the number of consecutive iterations having alternating error signs. Thus step 620 entails updating the S and O counts appropriately in view of the branch taken from step 606. In step 622, the S count is compared to a predetermined search threshold $S_T$. If the S count is greater than $S_T$ (i.e., "many" consecutive error signs have been the same), then the step size is increased in step 624. For example, the step size can be multiplied by a predetermined gain factor K greater than one. Whether or not the step size is increased in step 624, the next step increment $Z_{i+1}$ is computed in step 626. Step 626 sets the sign of the step depending on the sign of the error. Next, the stimulus is updated in step 628 according to $X_{i+1}=X_i+Z_{i+1}$, and this branch of the loop closes. As above, the loop can be initialized at any convenient point, such as 602.

Returning to step 606, suppose that the two error signs are different. Processing then follows the "no" path from step 606 to arrive at step 610. In step 610, the O count is incremented by one, and the S count is reset to zero. Thus step 610 also entails updating the S and O counts appropriately in view of the branch taken from step 606. In step 612, the O count is compared to a predetermined oscillation threshold $O_T$. If the O count is greater than $O_T$ (i.e., "many" consecutive error signs have alternated), then the step size is decreased in step 614. For example, the step size can be multiplied by a predetermined gain factor 1/K where K is greater than one. Whether or not the step size is decreased in step 614, the next step increment is computed in step 616. Step 616 sets the sign of the step depending on the sign of the error. Next, the stimulus is updated in step 618 according to $X_{i+1}=X_i+Z_{i+1}$, and this branch of the loop closes.

This control method is especially suitable for use with the present invention, since electrical cellular responses such as capture fraction are often highly quantized. Such quantization of a control variable makes conventional gradient estimation methods less appropriate than usual. In addition, cellular cultures can be noisy and significantly time-varying systems, both of which tend to complicate control. However, even though this control method is described in connection with closed loop control of cell cultures, it is applicable to any control application. Parameters such as $S_T$, $O_T$ and K can be adjusted empirically to fine-tune loop performance for various applications by a skilled art worker. In the examples of FIGS. 7, 8*a-b*, and 9*a-c*, $S_T=2$, $O_T=3$ and K=2.

Figure 7:
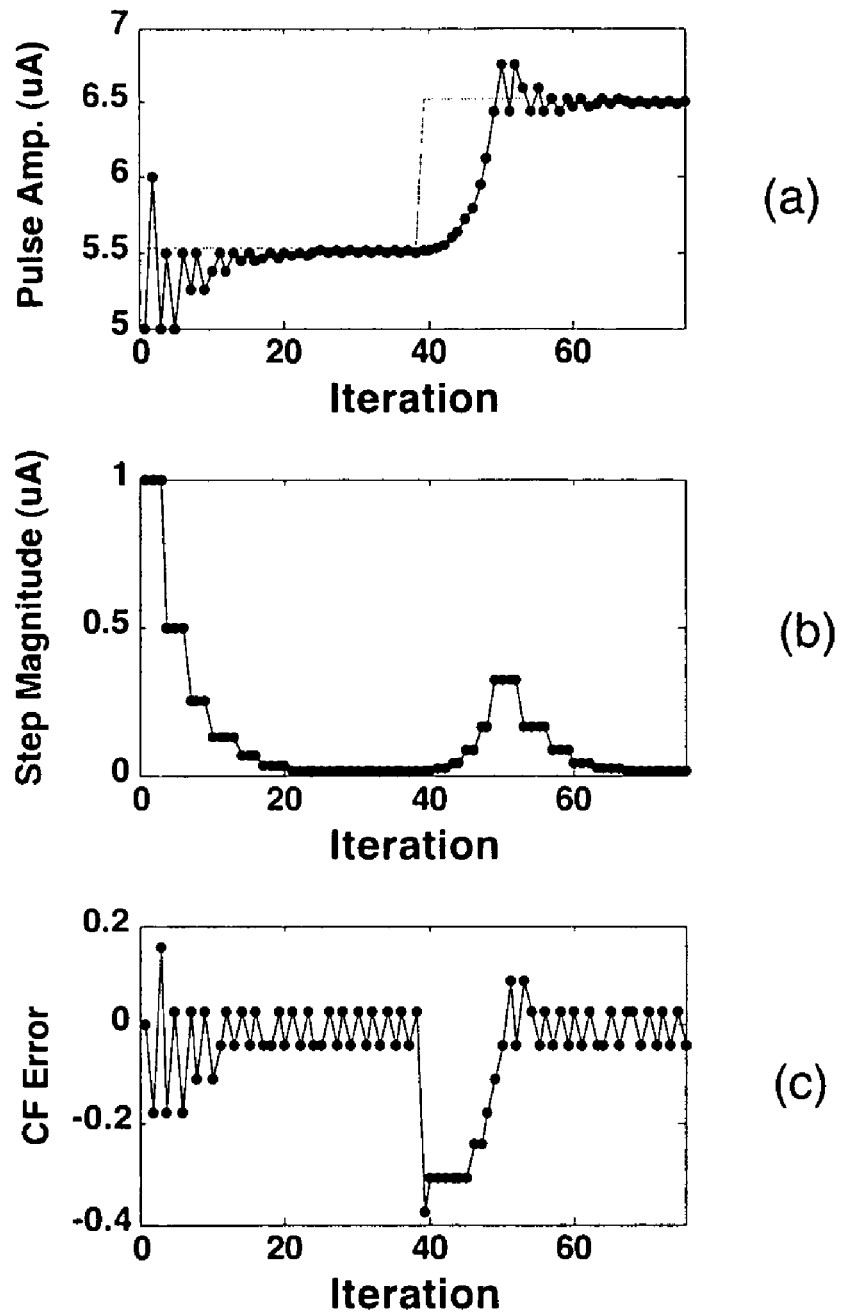
FIG. 7 shows simulation results pertaining to the method of FIG. 6.

FIG. 7 shows simulation results pertaining to the method of FIG. 6. Part (a) shows the stimulus control parameter (i.e., pulse amplitude) as a function of iteration number. A significant change in the simulated culture being controlled occurs at around iteration 40, such that the loop needs to settle to a new value. Initial convergence is seen, as is convergence to the post-change value. Convergence accuracy is about 0.01 µA. Part (b) shows the step magnitude as a function of iteration number. The decrease of step size as convergence is approached, as well as the increase in step size after the change are both apparent. In this example K=2, so a change in step size is either a doubling or a halving. Part (c) shows the error vs. iteration number. The error is relatively large because the simulated response is highly quantized.

Figure 8A:
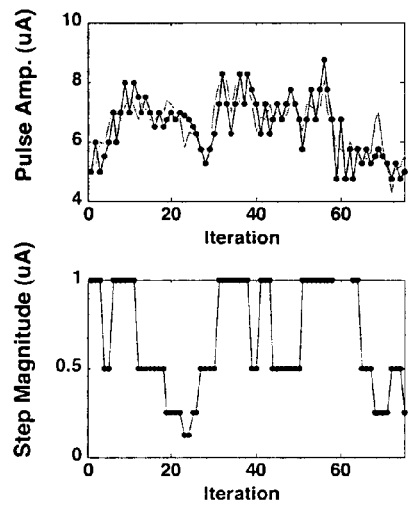
FIGS. 8a-b show simulation results pertaining to an embodiment of the invention making use of the updating method of FIG. 6.
Figure 8B:
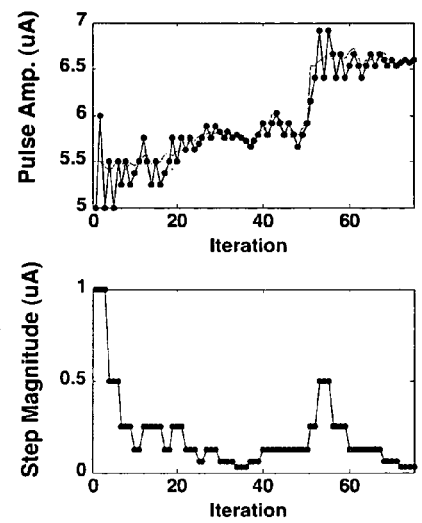

FIGS. 8*a-b* show simulation results pertaining to an embodiment of the invention making use of the updating method of FIG. 6. FIG. 8*a* shows results similar to those of FIG. 7, except that a significant level of noise (Brownian, normally distributed noise) is included in the simulation. The dotted line in the pulse amplitude plot of FIG. 8*a* is the value of the pulse amplitude that is required to set the cellular response (e.g., capture fraction) to a desired value (e.g., 0.5). Thus loop performance can be evaluated by how well the points track the dotted line.

Here several advantages of the method of FIG. 6 are more apparent. Since the method of FIG. 6 tends to increase step size in the presence of rapid parameter variations, the ability to rapidly follow such changes is improved. Furthermore, when parameters vary more slowly, the step size can decrease to improve accuracy. Finally, the control method is not particularly sensitive to the values of parameters $S_T$, $O_T$ and K, except that $S_T \geq K$ is preferred. The reason for this preference can be appreciated by considering a counter-example. Suppose K=20 and $S_T=2$. Then if two consecutive steps of size 1 are taken (total change is 2) with the same error sign, the next step will have size 20, which is 10× larger than the total change needed to trigger a larger step size. Such a large change in step size is likely to degrade loop performance.

FIG. 8*b* shows results similar to those of FIG. 8*a*, except that the noise level is reduced, and a sudden culture change is assumed at around iteration 50. The dotted line in the pulse amplitude plot of FIG. 8*b* is the value of the pulse amplitude that is required to set the cellular response (e.g., capture fraction) to a desired value (e.g., 0.5). The general behavior seen on FIG. 7 is also seen here, demonstrating efficient tracking of cell culture parameter changes in the presence of noise. More specifically, the step size is generally small, except at the beginning of the simulation and around iteration 50, where a sudden change occurred.

Figure 9A:
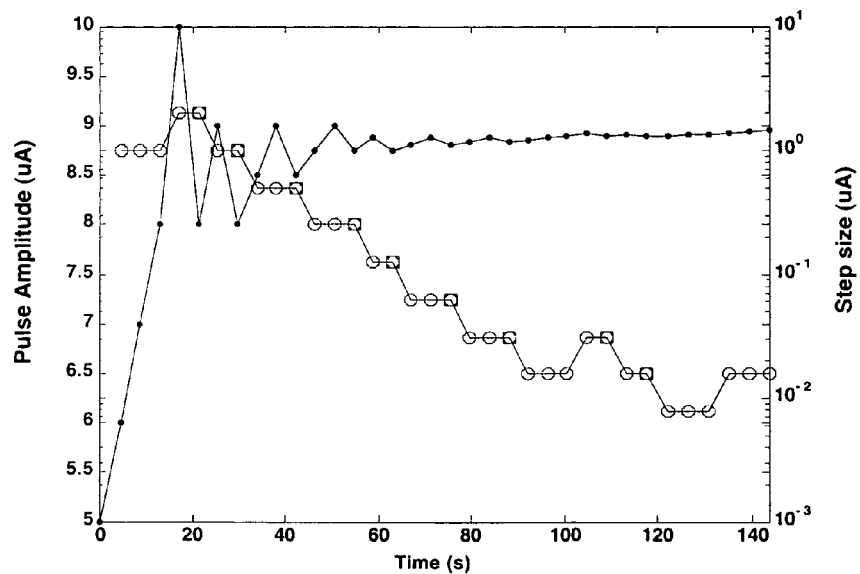
FIGS. 9a-c show measured results from an embodiment of the invention making use of the updating method of FIG. 6.
Figure 9B:
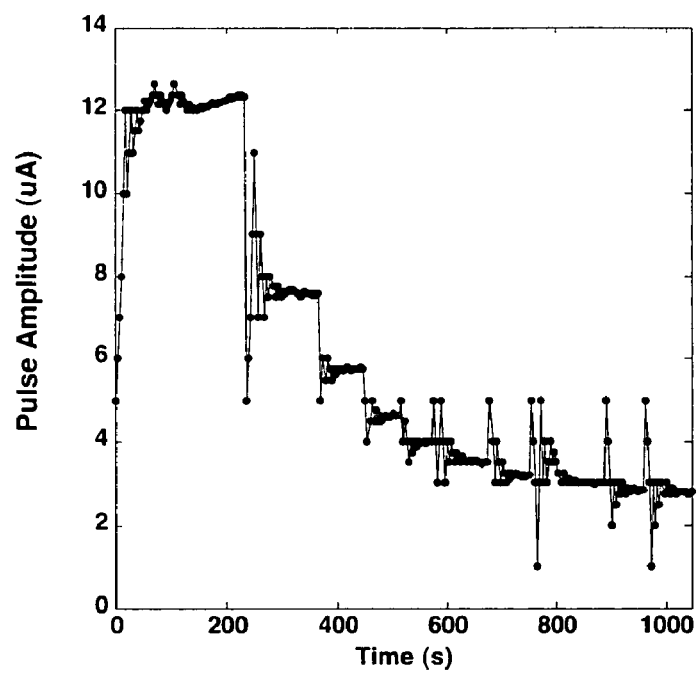
Figure 9C:
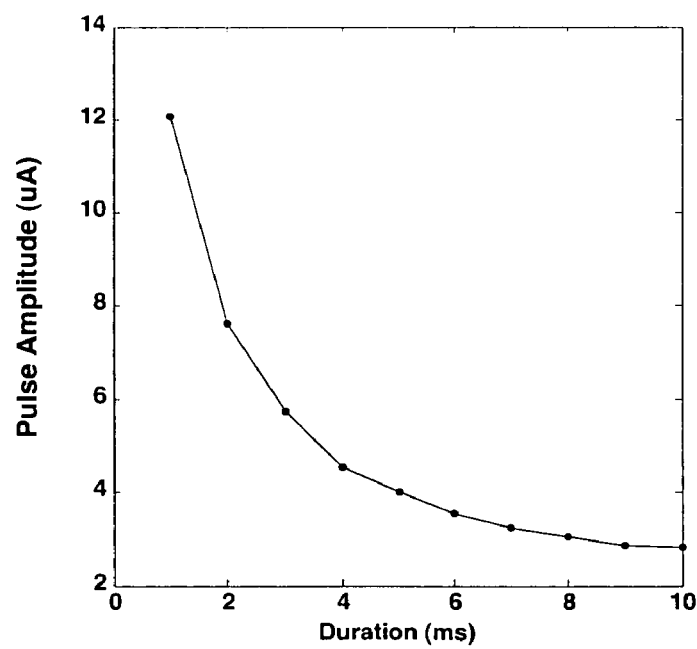

FIGS. 9*a-c* show measured results from an embodiment of the invention making use of the updating method of FIG. 6. A cardiac cell culture was placed under closed loop control (as on FIG. 1), using the control method of FIG. 6. Here the electrical stimulus parameter is pulse amplitude and the measured cellular response is capture fraction with a target value of 0.5. FIG. 9*a* shows measured pulse amplitude (black dots, left axis) and step size (circles and squares, right axis) under closed loop control. Convergence is obtained to a very high accuracy (i.e., within 0.01 µA), and this accuracy is obtained rapidly. In contrast, a traditional step-wise sweep of the parameter would have taken more than 5 minutes and would not have resolved the upward trend seen on FIG. 9*a* for times later than 80 s.

FIG. 9*b* shows an example of a capability provided by the present invention. As in FIG. 9*a*, the electrical stimulus parameter is pulse amplitude and the measured cellular response is capture fraction with a target value of 0.5. On FIG. 9*b*, the pulse duration is varied systematically while the control loop adjusts the pulse amplitude to maintain the capture fraction fixed to the target value of 0.5. Since the loop must converge before data can be read off, the rapid convergence provided by the invention is highly beneficial. Stepwise convergence is clearly visible on FIG. 9*b*.

FIG. 9*c* shows the resulting data as a strength-duration curve. Thus every point on the curve of FIG. 9*c* identifies a combination of pulse amplitude and pulse duration that provides a capture fraction of 0.5 for the culture under test. The effect of exposure of the cell culture to a drug or other compound (or more generally to any change in environment) can be evaluated by comparing strength-response data taken before an exposure to strength-response data taken after the exposure.

Figure 10:
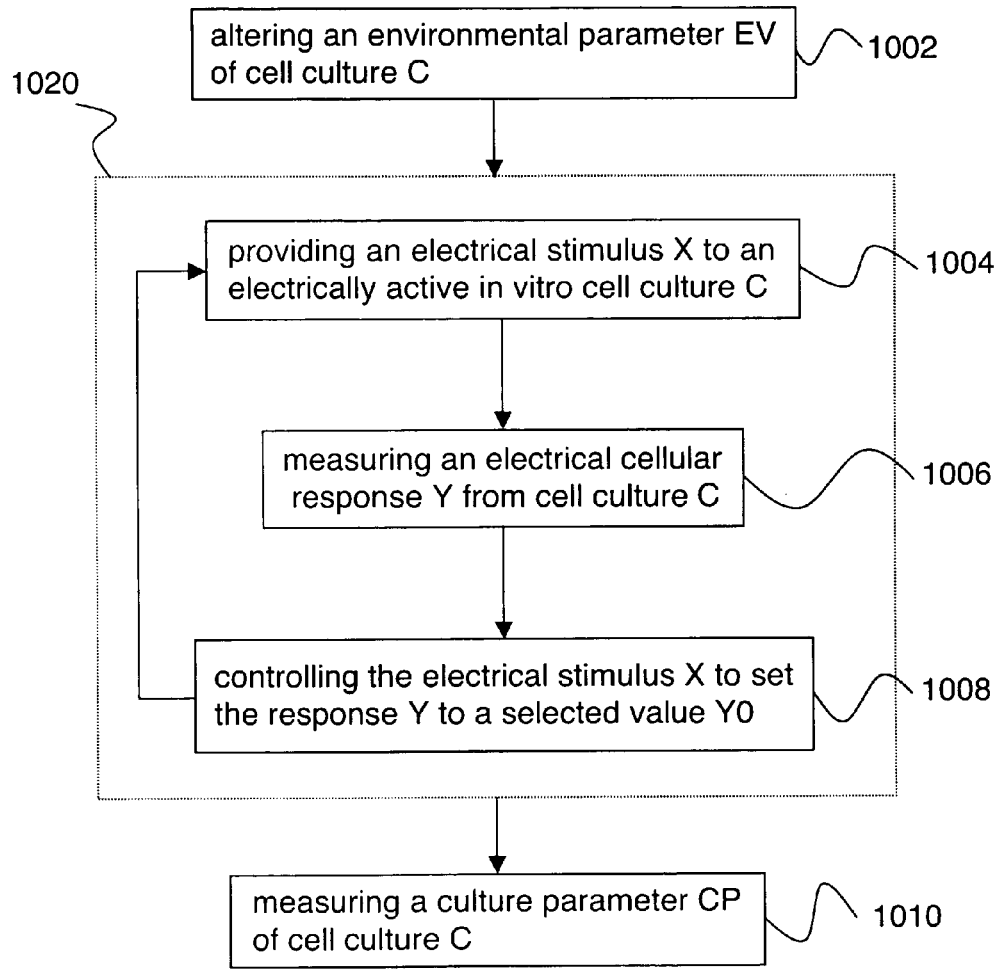
FIG. 10 is a block diagram of a method for measuring sensitivity of a cell culture to environmental changes according to an embodiment of the invention.

FIG. 10 is a block diagram of a method for measuring sensitivity of a cell culture to environmental changes according to an embodiment of the invention. Block 1020 on FIG. 10 includes steps corresponding to the steps of FIG. 1 for closed loop control of an electrically active cell culture. More specifically, step 1004 is applying an electrical stimulus to the cell culture, step 1006 is measuring an electrical response of the cell culture, and step 1008 is adjusting the stimulus to set the response to a selected value. The further steps of FIG. 10 are step 1002, where an environmental parameter EV of the cell culture is altered, and step 1010, where a culture parameter CP of the cell culture is measured. Frequently a time dependence of the culture parameter CP is measured.

The culture parameter can be the electrical stimulus of the control loop. Since the value of the electrical stimulus in closed loop operation depends on properties of the cell culture, such a stimulus is a culture parameter of the cell culture. Thus in preceding examples, if the pulse amplitude required to set the capture fraction to 0.5 is measured while the temperature of the culture is varied, temperature is the EV and pulse amplitude is the CP. The culture parameter can also be a parameter other than the electrical stimulus. In such cases, the culture parameter can be any measurable parameter (electrical or non-electrical) of the cell culture. Suitable culture parameters include: action potential amplitude; action potential duration; action potential waveform; conduction velocity; conduction direction; conduction speed; time delay between the stimulus and the response; impedance; capture fraction of stimulation; production of a protein; expression of a gene;

concentration of a chemical element or compound; and pH. Other suitable culture parameters include optical responses such as: radiation from a voltage-sensitive dye; radiation from an ion-sensitive dye; radiation from a fluorescent probe; and radiation from the cell culture. Here radiation refers generally to electromagnetic radiation, such as optical emission, light, etc.

The environmental parameter can be any parameter affecting the cell culture. Suitable environmental parameters include: concentration of a chemical element or compound; pH; mechanical stress; mechanical strain; acoustic radiation; temperature; electromagnetic radiation; particulate radiation; electric field; and magnetic field.

Figure 11:
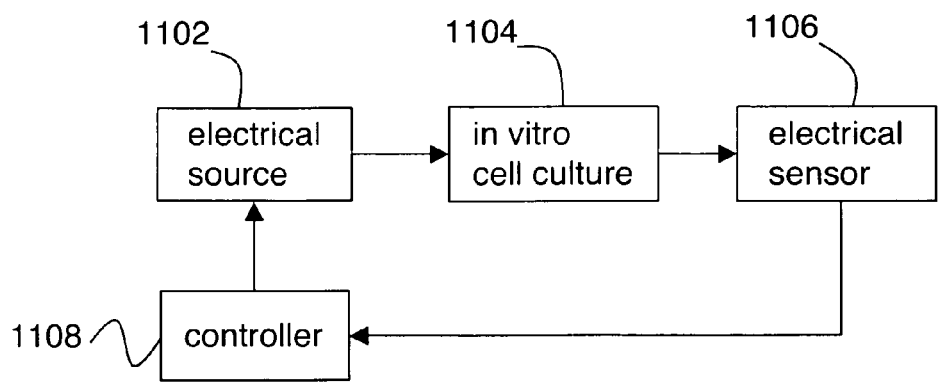
FIG. 11 shows a system for closed loop cell culture control according to an embodiment of the invention.

FIG. 11 shows a system for closed loop cell culture control according to an embodiment of the invention. An electrical source 1102 provides an electrical stimulus X to an in vitro cell culture 1104. Cell culture 1104 provides an electrical cellular response Y which is received by an electrical sensor 1106. Sensor 1106 provides a signal to a controller 1108. Controller 1108 controls the source to adjust the stimulus X such that the cellular response Y is set to a selected value Y0, as on FIG. 1. Both source 1102 and sensor 1106 typically include electrodes for making contact with cell culture 1104. The stimulus and sensing electrodes preferably include a microelectrode or microelectrode array (MEA), although any operative arrangement of stimulus and sensing electrodes is suitable for practicing the invention.

Figure 12:
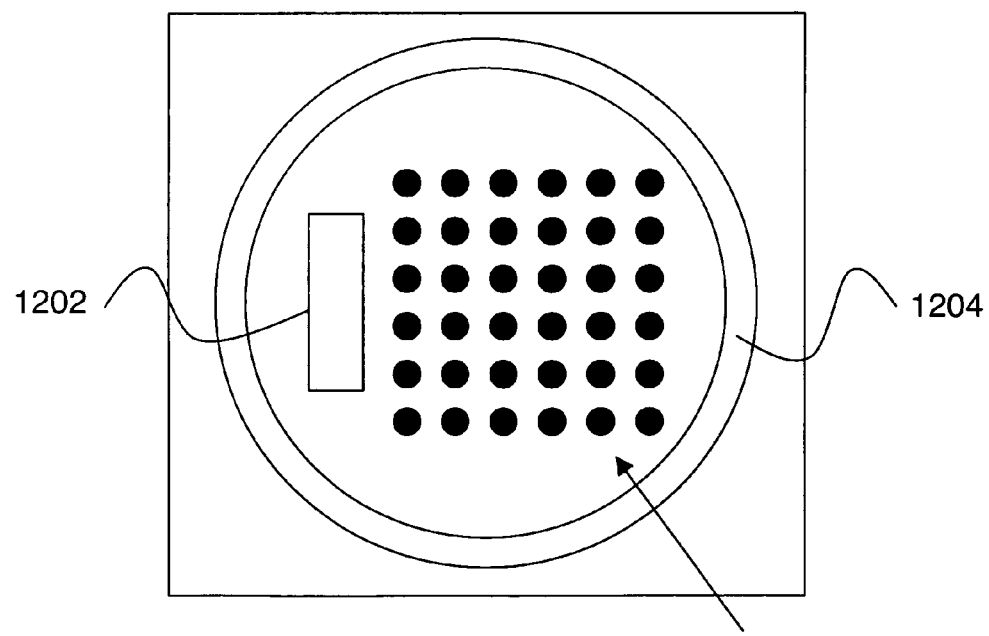
FIG. 12 shows an arrangement of electrodes suitable for practicing an embodiment of the invention.

FIG. 12 shows an arrangement of electrodes suitable for practicing an embodiment of the invention. In the example of FIG. 12, a microelectrode array (MEA) 1206 is disposed in proximity to a stimulus electrode 1202 and a ground electrode 1204. In this example, MEA 1206 is a 6×6 array of platinum electrodes having 22 μm diameter and 100 μm center to center spacing, and stimulation electrode 1202 is 100 μm by 200 μm. Preferably, a Platinum resistive thermal device (RTD) is integrated with the electrode array. This RTD provides real-time cell culture temperature measurements for continuous and precise monitoring and control of cell culture temperature. Such temperature control is important for accurate cell culture measurements. Conventional fabrication techniques are suitable for preparing such electrodes and temperature sensors. Ground electrode 1204 is preferably disposed in proximity to stimulus electrode 1202 and MEA 1206, as shown. Such proximity is helpful in reducing the magnitude of stimulation artifacts in the sensed response, and thereby reducing the tendency of response amplifiers to be driven into saturation. Although FIG. 12 shows a single stimulus electrode and multiple sensor electrodes, the invention is not so limited. In practicing the invention, one or more stimulus electrodes can be employed, and one or more sensor electrodes can be employed.

The preceding description has been by way of example as opposed to limitation. In particular, parameters relating to control loops or signal processing steps, such as thresholds, time windows, etc. are provided as examples. Such parameters can be modified to suit particular applications by a skilled art worker based on the described principles to practice the invention. Similarly, detailed apparatus dimensions and configurations are also provided as examples, and can be modified for other applications.

The invention is compatible with various methods of cell culture perfusion. More specifically, the cell culture can be perfused with a circulating cell culture medium, or the cell culture can be placed in a non-circulating bath of medium. Use of a circulating medium is preferred. In either case, any parameter of the cell culture medium is suitable for use as an environment parameter according to the invention. For example, a compound can be added to or removed from the cell culture, or can have its concentration in the cell culture altered from one value to another value.

The invention claimed is:

1. A method for measuring a response of a cell culture to changes in an environmental parameter of the cell culture, the method comprising:
  a) providing a multi-cell, in vitro, electrically active cell culture having an electrical cellular response to an electrical stimulus, wherein the cellular response is a collective response of the cell culture to the electrical stimulus;
  b) providing the electrical stimulus to the cell culture;
  c) measuring the electrical cellular response of the cell culture to the electrical stimulus;
  d) providing an automatic closed loop control system that automatically controls the electrical stimulus to set the measured electrical cellular response to a selected value;
  e) recording a time dependence of a culture parameter of the cell culture; and
  f) altering the environmental parameter of the cell culture.

2. The method of claim 1, wherein said cell culture comprises cardiac tissue.

3. The method of claim 1, wherein said electrical cellular response is a response of substantially all of said cell culture.

4. The method of claim 1, wherein said electrical cellular response is a response of a fraction of said cell culture.

5. The method of claim 1, wherein said electrical cellular response is voltage waveform.

6. The method of claim 1, wherein said electrical cellular response comprises efficacy of said stimulus for producing an electrical response.

7. The method of claim 1, wherein said providing the electrical stimulus comprises providing charge-balanced electrical pulses.

8. The method of claim 1, wherein said measuring the electrical cellular response comprises:
  a) detecting events;
  b) classifying the detected events as stimulation artifact events or non-artifact events based on temporal coincidence;
  c) selecting a threshold;
  d) nulling and padding detected events which are beyond said selected threshold and which are classified as stimulation artifact events to provide a modified data stream; and
  e) filtering the modified data stream.

9. The method of claim 8, wherein said threshold is selected to maximize a number of non-artifact events.

10. The method of claim 8, wherein said selecting a threshold comprises selecting the threshold from a predetermined set of threshold values.

11. The method of claim 1, wherein said controlling comprises altering a stimulus parameter selected from the group consisting of: amplitude; duration; waveform; polarity; pulse rate; pulse train duration; multi-electrode timing; and multi-electrode spatial pattern.

12. The method of claim 1, wherein said controlling comprises:
  a) calculating a new step increment proportional to a product of a current step increment and an error signal;
  b) incrementing the electrical stimulus by the new step increment.

13. The method of claim 1, wherein said controlling comprises:
  a) incrementing the electrical stimulus by a step increment having a sign dependent on a difference between said measured electrical cellular response and said selected value;
  b) increasing a magnitude of the step increment if the difference has the same sign for a number of consecutive iterations greater than a predetermined search threshold; and
  c) decreasing the magnitude of the step increment if the difference has an alternating sign for a number of consecutive iterations greater than a predetermined oscillation threshold.

14. The method of claim 1, wherein said culture parameter is said electrical stimulus.

15. The method of claim 1, wherein said culture parameter is action potential waveform.

16. The method of claim 1, wherein said culture parameter is a response from a voltage-sensitive dye, an ion-sensitive dye or from a fluorescent probe.

17. The method of claim 1, wherein said environmental parameter is concentration of a chemical element or compound.

* * * * *